United States Patent [19]

Shinpo et al.

[11] Patent Number: 4,738,838

[45] Date of Patent: * Apr. 19, 1988

[54] SILICA BASE FOR DENTIFRICE AND PROCESS FOR ITS PREPARATION

[75] Inventors: Shozo Shinpo, Kako; Tetsuo Fushino, Takasago; Akihiro Hachijo, Kobe; Shozo Ohtsu, Kakogawa, all of Japan

[73] Assignee: Taki Chemical Co., Ltd., Hyogo, Japan

[*] Notice: The portion of the term of this patent subsequent to Apr. 8, 2003 has been disclaimed.

[21] Appl. No.: 906,013

[22] Filed: Sep. 11, 1986

Related U.S. Application Data

[62] Division of Ser. No. 666,955, Oct. 17, 1984, abandoned.

[30] Foreign Application Priority Data

Mar. 4, 1983 [JP] Japan ................................. 58-36283

[51] Int. Cl.$^4$ ............................................. C01B 33/12
[52] U.S. Cl. ..................................... 423/339; 423/338
[58] Field of Search ................................. 423/338, 339

[56] References Cited

U.S. PATENT DOCUMENTS

| | | | |
|---|---|---|---|
| 3,041,140 | 6/1962 | Alexander | 423/335 |
| 3,607,777 | 9/1971 | Winyall et al. | 423/338 |
| 3,893,840 | 7/1975 | Wason | 423/339 |
| 4,010,160 | 3/1977 | Iler | 423/335 |
| 4,010,242 | 3/1977 | Iler | 423/335 |
| 4,038,098 | 7/1977 | Wason | 423/339 |
| 4,122,160 | 10/1978 | Wason | 423/335 |
| 4,251,281 | –2/1981 | Machurat et al. | 423/339 |
| 4,272,509 | 6/1981 | Wason | 423/339 |
| 4,279,766 | 7/1981 | Joubert | 423/335 |
| 4,457,900 | 7/1984 | Steen | 423/335 |
| 4,508,607 | 4/1985 | Winyall | 423/335 |
| 4,581,217 | 4/1986 | Shinpo et al. | 423/339 |
| 4,581,292 | 4/1986 | Shinpo et al. | 428/402 |

FOREIGN PATENT DOCUMENTS

| | | | |
|---|---|---|---|
| 5125235 | 12/1964 | Japan | 423/339 |
| 429767 | 5/1967 | Japan | 423/339 |
| 0004919 | 3/1979 | Japan | 423/339 |
| 0116613 | 9/1980 | Japan | 423/339 |
| 2125780 | 3/1984 | United Kingdom | 423/338 |

*Primary Examiner*—John Doll
*Assistant Examiner*—Lori S. Freeman
*Attorney, Agent, or Firm*—Wenderoth, Lind & Ponack

[57] ABSTRACT

Silica base material for dentifrice having excellent transparency, prolonged stability, and desired abrasiveness; has a specific surface area of 270–500 m$^2$/g as measured by BET method and 5–60 m$^2$/g by CTAB method, gives virtually amorphous X-ray diffraction pattern after firing at 1100° C., and has a refractive index of 1.455–1.470. This base material can be prepared by reacting an alkali metal silicate solution with hydrochloric acid or sulfuric acid in the presence of an electrolyte, controlling the ratio of the rate of addition of chloride ion or sulfate ion to be at least 3:2 between the acidification stage in which the pH at the completion of the reaction is brought to 3.5 or less, and the silica crystallization stage in which the pH of the reaction system if brought to 10.0, and carrying out the acidification stage within 30 minutes.

9 Claims, No Drawings

SILICA BASE FOR DENTIFRICE AND PROCESS FOR ITS PREPARATION

This application is a division of Ser. No. 666,955 filed Oct. 17, 1984, now abandoned.

TECHNICAL FIELD

This invention relates to a silica base material for dentifrice formulation, particularly to one for transparent dentifrice formulation, which gives an outstanding, stable transparency yet with a desired abrasiveness.

BACKGROUND ART

Of late years transparent dentrifice formulations of various types have been developed and put on the market, giving a favorable impression with their freshness and cleanliness associated with the transparency.

For transparent dentifrice formulations there has been used in the past a silica base material which can impart transparency to the dentifrice formulation, but has no substantial abrasiveness so that the resulting dentifrice has not been satisfactory in actual use as a dentifrice. Further, it has also been proposed to use a silica base material which has a refractive index which is close to that of the transparent dentifrice vehicle used for formulation into a transparent dentifrice, but the known silica base material has a refractive index that shows fluctuation and is poor in stability so that it is difficult to obtain a transparent dentifrice with good stability.

Meanwhile, several methods have been proposed to produce silica base materials having appropriate abrasiveness for transparent formulation. For example, Japanese Patent Publication No. '74-11159 describes a method wherin a commercial superfine amorphous silica devoid of abrasiveness and therefore unsuitable for dentifrice base material is wetted with water or a dilute aqueous solution of inorganic alkali metal salt, fired at 500°–1000° C., and then ground. It is true that this method provides abrasiveness needed by a dentifrice base material. But the abrasiveness thus provided is often so much in excess as to damage tooth enamel and the material itself does not give good transparency and consistent stability. Finally, it would be hard to industrialize the method economically.

Another method is described in Japanese Patent Kokai Nos. '76-12869 and '76-136841 to provide abrasiveness to silica. The material obtained by this method, however, does not give good paste stability when combined with a transparent dentifrice vehicle.

The invention described in Japanese Patent Publication No. '73-14935 discloses a transparent dentifrice formulation containing silica specified as follows:
refractive index: 1.40–1.47
oil absorption: 1.5 cc and less
particle size: ca. 0.01–0.5$\mu$
The silica prepared by the method disclosed in this publication gives a BET surface area of 150 m$^2$/g, and a CTAB surface area of 82 m$^2$/g. When this silica is mixed with humectant and left to stand, the turbidity of the mixture, or paste, grows markedly from day to day and the paste stability is gradually worsened.

In addition, one of the present inventors disclosed in Japanese Patent Publication Nos. '74-8640 and '77-15078 a method to control the refractive index of silica by allowing fluoride ion to intervene in the proposed process. The product of this invention as a base material for transparent dentifrice formulation was still not without a problem in transparency and was not as stable as expected.

Thus the silicas publicly known heretofore have defects either in abrasiveness, stability or transparency which are the essential characteristics of the base material for transparent dentifrice formulation, and therefore none of them are satisfactory for such formulation.

Years of intensive study on these essential characteristics of silica base material has now revealed to the present inventors that combinations of a tooth-paste vehicle with the silica base material of the present invention, as described in detail below, can bring forth a transparent dentifrice formulation with proper abrasiveness, water-like transparency and good long-term stability under storage.

Transparency as referred to in this invention is defined and measured as follows: two solutions or different refractive indices like glycerine and water are mixed in various proportions to give dispersion media of different refractive indices; a fixed amount of silica base material is then mixed with a fixed amount of each medium into a dispersion, which, as needed, is deaerated and subjected to measurement of refractive index and turbidity; and with these as parameters a curve is plotted to determine the minimum turbidity point which represents the transparency here.

The present inventors studied in detail the factors influencing the transparency and, finding that the porosity of silica base material is greatly involved, came to accomplish the invention.

DISCLOSURE OF THE INVENTION

Namely, the invention relates to a silica base material for dentifrice formulation characterized by having a specific surface area by the BET method of 270–500 m$^2$/g-anhydride, and by the CTAB method of 5–60 m$^2$/g-anhydride; giving virtually amorphous X-ray diffraction patterns after firing at 1100° C.; and having a refractive index of 1.455–1.470.

Now before proceeding further, explanations will be given here on the terminology covering specific surface area by the BET method, specific surface area by the CTAB method, refractive index, X-ray diffraction after firing at 1100° C., and loss by abrasion, or abrasiveness.

(1) Measurement of specific surface area by the BET method.

With Liquid nitrogen as coolant, the adsorption in quantity of nitrogen gas by sample is measured at −196° C.; the surface area per one gram of sample in anhydride form is then calculated, based on the molecular cross-section of nitrogen, 16.2 Å$^2$. Deaeration of the sample is conducted at 140° C. under vacuum of $1 \times 10^{-5}$ mmHg for 60 minutes.

(2) Measurement of specific surface area by the CTAB method.

Cetyl methyl ammonium bromide is allowed to be adsorbed onto the sample until saturation from its aqueous solution; the surface area per gram of sample in anhydride form is then calculated, based on the molecular cross-section of the bromide, 35 Å$^2$.

Procedure: Take 1 g of sample of known moisture content in a 300 ml conical flask having a common stopper. Add 100 ml of 0.55% solution of CTAB and bring the pH of the mixture to 9.0 with 0.1N NaOH solution. Keep agitating for 2 hours with a magnetic stirrer. Settle the suspension centrifugally and transfer 10 ml of the supernatant into a 300 ml conical flask. Add 50 ml of demineralized water, 25 ml of chloroform, drops of bromophenol blue indicator and titrate it with sodium dioctyl sulfo succinate (Aerosol OT) solution previously calibrated by a standard CTAB solution. End the titration when the chloroform layer is decolorized while the aqueous layer is slightly tinged purple. Mark the consumption in ml of Aerosol OT as $V_2$.

Then conduct a blank titration in a similar manner on 10 ml of the first CTAB solution only and mark the Aerosol OT consumption in ml as $V_1$.

Calculate the surface area per gram of anhydrate ($Sm^2/g$) by the following equation.

$$S = \frac{5.78 \times (V_1 - V_2) \times a}{X}$$

Wherein
X = sample weight as anhydrate (g);
a = CTAB in weight (mg) equivalent to 1 ml of the Aerosol OT solution (3) Refractive index Mix glycerine and water in various proportions to obtain dispersing media of different refractive indices. Disperse 15 g of sample in 35 g of each medium, using a vacuum mortar-mixer for 10 minutes.

Measure the refractive index and turbidity of the mixture at 25° C. and plot the data to obtain a refractive index-turbidity curve. Represent the sample by the refractive index of the mixture at the lowest turbidity point. In these measurements use an Abbe's refractometer and an integration sphere turbidimeter; and determine turbidity from the transmittancy at sample thickness of 1 mm.

(4) X-Ray diffraction after firing at 1100° C.

Take about 5 g of sample on a platinum plate and fire it at 1100° C. for an hour in an electric furnace. Then examine it on a X-ray diffractometer.

(5) Abrasiveness

Use an abrasion tester of horizontal brushing movement; of a suspension of 25% silica fine powder in 60% glycerine/water solution, take some and put it on the flat face of the bronze plate; with the testing load, or weight of 500 g on it, conduct the brushing 1800 times; then measure the weight loss of the bronze plate for abrasiveness.

The word "anhydride" as used in this invention shall refer to a form or state of finely ground silica dried up to nearly constant weight at 105° C. for two hours.

Now the method for making the silica base material for dentifrice formulation of this invention will be described in detail.

The alkali metal silicate used in the invention includes sodium, potassium and lithium silicate, but more preferred of these is sodium silicate because it is less costly. Silicates having a molar ratio, $SiO_2/X_2O$, (wherein X denotes alkali metal,) of 2-4 can be used. The acidifying agent used in this invention is hydrochloric or sulfuric acid.

The preferable $SiO_2$ concentration of the alkali metal silicate solution at the stage of acidification with such acid is 5-15% by weight and the preferable acid concentration is also 5-15% by weight; and in proper combination with other reaction parameters the acid and silicate concentrations within such ranges can bring forth the desired properties of silica base material.

The electrolytes preferred in this invention are alkali metal salts of mineral acid such as sodium chloride, potassium chloride, sodium sulfate, potassium sulfate, sodium carbonate, potassium carbonate, sodium nitrate and potassium nitrate, to name only sodium and potassium salts as typical examples. The electrolyte is used in the range of 10-60% by weight of $SiO_2$, as required, considering the abrasiveness of silica base material.

In the present invention the alkali metal silicate solution is first made to react with hydrochloric or sulfuric acid under the presence of such electrolyte.

The preferred manner of performing the reaction is to mix the electrolyte previously with the alkali metalsilicate solution, in view of giving the abrasiveness to silica base material. However, it is also acceptable to add the electrolyte, in consideration of its quanity, reaction temperature, reaction time, etc., to hydrochloric or sulfuric acid in advance. In said preferred manner also it is well to charge the reactor with alkali metal silicate solution and electrolyte solution simultaneously or separately, or it is as well to mix these two solutions prior to the introduction into the reactor.

It is preferable to conduct the reaction under good agitation in a temperature range of 60°-100° C.

The essence of the production method of silica base material disclosed herein lies in the fact that the reaction is conducted in two stages; the silica crystallization stage for which the pH of the reaction mixture is brought to 10.0, and the acidification stage for which the pH is finally brought down to 3.5 or less; the ratio of the rate of addition of chloride or sulfate ion in the acidification stage to the rate of said addition in the silica crystallization stage is at least 3:2; and the acidification is carried out within 30 minutes.

The silica crystallization stage herein means the stage of reaction where more than 95% of silica content (as $SiO_2$) in the alkali metal silicate solution is crystallized out. It is preferable to conduct this part the reaction to take 40 minutes to 4 hours. Meanwhile, the acidification stage is the stage of reaction ranging from the point where most of the silica has crystallized out at the reaction pH of 10.0 to the point where the pH has been brought down to 3.5 or less by adding hydrochloric or sulfuric acid. Taking too long in the acidification somehow makes it difficult to obtain silica base material of excellent transparency and good abrasiveness.

The present inventors, therefore, studied further for a method devoid of such a defect, which would give a variety of silica base material of low to high abrasiveness for transparent formulation, and found that it is necessary to perform the acidification stage within 30 minutes and that the ratio of the rate of addition of hydrochloric or sulfuric ion between the acidification and silica crystallization stages should be at least 3:2.

Namely, shortening the acidification stage led to remarkable improvements in the characteristics of silica base material and its productivity.

When the pH of reaction mixture in the acidification stage is made 3.5 or less, or more specifically, 1.5-3.0, the refractive index of the resulting silica base material can be brought within a narrow range of 1.455-1.470. When the reaction pH exceeds 3.5, silica base material good for transparent formulation can not be obtained because of the scattering of refractive indices.

After the acidification stage, ageing may be performed for 10 minutes or longer but is not a requisite.

The rest of the operation is to filter, wash, dewater, dry and grind the silica base material in the usual manner.

The silica base material thus obtained has a specific surface area by the BET method of 270–500 m$^2$/g-anhydride and also one by the CTAB method of 5–60 m$^2$/g-anhydride; it gives amorphous X-ray diffraction patters after firing at 1100° C.; and it has a refractive index of 1.455–1.470.

The product shows good transparency indicated by the lowest turbidity of 0.05 or less and a long-term stability. The abrasiveness of the product can be changed freely within the range of 2–90 mg.

Thus the product is a useful base material particularly for transparent dentifrice formulations.

Described above is one of the processes for producing silica base material for transparent dentifrice formulations, and it is also possible to obtain by different processes silica base material having a specific surface area by the BET method of 270–500 m$^2$/g-anhydride and also one by the CTAB method of 5–60 m$^2$/g-anhydride, giving amorphous X-ray diffraction patterns after firing at 1100° C. It is clear that the thus obtained base material has excellent transparency and stability over time. Furthermore, in the production of the silica herein, it is, of course, possible to use and add, for the purpose of adjusting abrasiveness or as refractive index controlling agent, to the alkali metal silicate solution, hydrochloric acid or sulfuric acid and others, or while in the reaction stage, aluminum sulfate, aluminum chloride, calcium chloride, magnesium chloride, basic salts of these compounds, sodium fluoride, potassium fluoride, ammonium fluoride and others.

Now, the features of silica base material for dentifrice formulations of this invention will be better clarified through the examples shown below:

Reference 1

Into a 20 l reactor equipped with a bafle plate and an agitator with 150 mm D turbine blades was introduced 10 kg of an aqueous solution of sodium silicate (Na$_2$O.3.2SiO$_2$) containing 90 g/kg of SiO$_2$ and then, under the reaction temperature kept at 50° C., 9.0% sulfuric acid at the flow rate of 85 g/min for 42 minutes to bring the pH of reaction mixture to 10.0. Then the addition of 9.0% sulfuric acid was continued at the flow rate of 135 g/min until 10 minutes later when the pH reached 5.8. The acid was stopped and the reaction mixture was allowed to stand for ageing for 15 minutes. After repeated filtration and washing, the obtained solid was dried in a hot air oven at 110° C. and finely ground.

The fine silica powder thus obtained had a specific surface area by the BET method of 295 m$^2$/g and by the CTAB method of 218 m$^2$/g; it gave α-cristobalite X-ray diffraction patterns after being fired at 1100° C. The fine silica powder thus obtained had a poor abrasiveness and, when it was used for toothpaste, increased the viscosity. Thus, silica of this kind was found not to be usable for toothpaste in its preparation.

Reference 2

Into a reactor used in reference 1 was introduced 10 kg of an aqueous solution of sodium silicate (Na$_2$O..2.8SiO$_2$) containing 110 g/kg of SiO$_2$ and 4 g/kg of NaCl and then, under the reaction temperature kept at 65° C., 10% sulfuric acid at the flow rate of 107 g/min for 63 minutes to bring the pH of the reaction mixture to 2.1. Acid addition was stopped and the mixture was then allowed to stand for ageing for 30 minutes. After repeated filtration and washing, the wet cake was dried in a hot air oven at 110° C. and finely ground.

The fine silica powder thus obtained has a specific surface area by the BET method of 380 m$^2$/g and by the CTAB method of 152 m$^2$/g; it gave an amorphous X-ray diffraction pattern after being fired at 1100° C. This silica had good transparency as base material for transparent dentifrice formulation but gave poor abrasiveness to the toothpaste product.

Reference 3

Into a reactor used in reference 1 was introduced 10 kg of an aqueous solution of sodium silicate (Na$_2$O.3.1SiO$_2$) containing 100 g/kg of SiO$_2$ and 15 g/kg of NaCl and then, under the reaction temperature kept at 75° C., 10% sulfuric acid at the flow rate of 44 g/min for 84 minutes to bring the pH of reaction mixture to 10.0. Then the addition for 10% sulfuric acid was continued at the flow rate of 148 g/min until 10 minutes later when the pH reached 4.5. The acid was stopped and the reaction mixture was allowed to stand for aging for 20 minutes. After repeated filtration and washing, the obtained solid was dried in a hot air oven at 110° C. and finely ground.

The fine silica powder thus obtained had a specific surface area by the BET method of 196 m$^2$/g and by the CTAB method of 42 m$^2$/g; it gave α-cristobalite X-ray diffraction pattern after being fired at 1100° C. This silica had comparatively high abrasiveness as base material for dentifrice formulations, but the product made from this silica showed high turbidity and poor long-lasting transparency, and thus, this silica is not of such quality as can be used for transparent toothpaste as base material.

Reference 4

Into a reactor used in reference 1 was introduced 10 kg of sodium silicate solution (Na$_2$O.3.1SiO$_2$) containing 100 g/kg of SiO$_2$ and 15 g/kg of NaCl and then under the reaction temperature kept at 75° C., 10% sulfuric acid at the flow rate of 148 g/min for 25 minutes to bring the pH of the reaction mixture to 10.0. Then the addition of 10% sulfuric acid was continued at the flow rate of 44 g/min until 35 minutes later when the pH reached 4.6. The acid was stopped and the reaction mixture was allowed to stand for ageing for 20 minutes. After repeated filtration and washing, part of the wet cake was dried in a hot air oven at 110° C. and finely ground.

The fine silica powder thus obtained had a specific surface area by the BET method of 224 m$^2$/g and by the CTAB method of 103 m$^2$/g; it gave an α-cristobalite X-ray diffraction pattern after being fired at 1100° C. It had less abrasiveness as compared with silica produced in reference 3, also has poor long-lasting transparency, thus not being suitable for transparent dentifrice formulation as base material.

Reference 5

Into a reactor used in reference 1 was introduced 10 kg of an aqueous solution of sodium silicate (Na$_2$O.3.2SiO$_2$) containing 95 g/kg of SiO$_2$ and 25 g/kg NaCl and then, under the reaction temperature kept at 87° C., 10% sulfuric acid at the flow rate of 34 g/min for 100 minutes to bring the pH of reaction mixture to 10.0. Then the addition of 10% sulfuric acid was continued at the flow rate of 78 g/min until 18 minutes later when the pH reached 3.9. The acid was stopped and the reaction mixture was allowed to stand for ageing for 15 minutes. After repeated filtration and washing, the obtained solid was dried in hot air oven at 110° C. and finely ground.

The fine silica powder thus obtained has a specific surface area by the BET method of 207 m²/g and by the CTAB method of 26 m²/g; it gave α-cristabalite X-ray diffraction pattern after being fired at 1100° C. This silica base material proved to be a product of sufficient abrasiveness to meet requirements of base material for toothpaste but of high turbidity and giving poor transparency over time, and is not suited for silica base material for transparent dentrifrice formulation.

peated filtration and washing, the wet cake was dried in a hot air oven at 110° C. and finely ground.

The fine silica powder thus obtained had a specific surface area by the BET method of 342 m²/g and by the CTAB method of 39 m²/g; it gave an amorphous X-ray diffraction pattern after being fired at 1100° C. It proved to be a product of moderate abrasiveness, good transparency and long-lasting transparency.

Table 1 shows the physical properties of the products produced above.

TABLE 1

| Reference | BET method surface area (m²/g) | CTAB method surface area (m²/g) | X-ray diffraction | Abrasiveness (mg) | Turbidity just after mixed | Turbidity 5 days after mixed | Refractive index |
|---|---|---|---|---|---|---|---|
| 1 | 295 | 218 | α-cristabalite | 0.2 | 0.15 | 0.37 | 1.444 |
| 2 | 380 | 152 | amorphous | 0.5 | 0.02 | 0.03 | 1.462 |
| 3 | 196 | 42 | α-cristabalite | 8.3 | 0.63 | 0.85 | 1.450 |
| 4 | 224 | 103 | α-cristabalite | 1.2 | 0.19 | 0.42 | 1.456 |
| 5 | 207 | 26 | α-cristabalite | 24.3 | 0.42 | 0.68 | 1.455 |
| 6 | 82 | 17 | α-cristabalite | 37.4 | 0.95 | 0.96 | impossible to measure |
| 7 | 80 | 40 | α-cristabalite | 17.8 | 0.21 | 0.46 | 1.457 |
| Example of this invention | 342 | 39 | amorphous | 20.9 | 0.04 | 0.04 | 1.460 |

Reference 6

Into a reactor used in reference 1 was introduced 10 kg of sodium silicate solution ($Na_2O \cdot 3.1SiO_2$) containing 110 g/kg of $SiO_2$ and 40 g/kg of NaCl and then under the reaction temperature kept at 80° C., 10% sulfuric acid at the flow rate of 47 g/min for 120 minutes to bring the pH of the reaction mixture to 5.6. The mixture was then allowed to stand for ageing for 30 minutes. After repeated filtration and washing, the wet cake was dried in a hot air oven at 110° C. and finely ground.

The fine silica powder thus obtained has a specific surface area by the BET method of 82 m²/g and by the CTAB method of 17 m²/g; it gave an α-cristabalite X-ray diffraction pattern after being fired at 1100° C. This silica had high abrasiveness, but was not suited for transparent dentifrice formulation as base material due to lack of transparency.

Reference 7

A commercially available silica base material for toothpaste made in the USA was evaluated for physical properties. As a result, it was found that it had specific surface area by the BET method of 80 m²/g and by the CTAB method of 40 m²/g, giving α-cristabalite X-ray diffraction pattern after being fired at 1100° C.

It proved to be a product of moderate abrasiveness but of high turbidity of 0.21 and presenting poor transparency over time.

Example of this invention

Into a reactor used in reference 1 was introduced 10 kg of sodium silica solution ($Na_2O \cdot 3.1SiO_2$) containing 95 g/kg of $SiO_2$ and 20 g/kg of NaCl and then under the reaction temperature kept at 87° C., 10% sulfuric acid at the flow rate of 37 g/min for 95 minutes to bring the pH of the reaction mixture to 10.0. Then the addition of 10% sulfuric acid was continued at the flow rate of 82 g/min until 19 minutes later when the pH reached 3.1. The acid was stopped and the reaction mixture was allowed to stand for ageing for 30 minutes. After re- As described in references Nos. 1 to 7 and the example of the present invention, three parameters of the BET specific surface area, the CTAB specific surface area and X-ray diffraction pattern after firing at 1100° C. are important factors for determining such physical properties of silica base material for transparent dentifrice formulations as transparency, abrasiveness and long-lasting transparency of the toothpaste product. A silica failing to satisfy said three parameters is not desirable as silica base material for toothpaste, particularly for transparent dentrifrice formulations.

When the silica base material of the present invention is used in a transparent toothpaste formulation, the base material is mixed and kneaded with a transparent paste vehicle. In order to give proper fluidity to such toothpaste formulation, the paste vehicle is chosen from humectants and binders. Among humectants there are, for example, glycerine, sorbitol, polyethylene glycol, dextrine, propylene glycol, etc., and for binders there are carboxymethyl cellulose, sodium alginate, etc. Toothpaste formulations containing such humectants or binders and other ingredients such as cleaning agent, perfume, sweetening agents, enzyme and various medicinal adjuvants are widely known to those experienced in the art.

As is understood from the explanation given, the silica base material of the present invention is most effectively used in the production of transparent toothpaste of desired abrasiveness.

The invention will be further explained by way of examples, which in no way shall be construed to limit the scope of the invention.

In the following examples, percentages shall denote percentages by weight unless otherwise specified.

EXAMPLE 1

Into a 5 m³ reactor equipped with a baffle plate and an agitator with 850 mm D turbine blades was introduced 2775 kg of an aqueous solution of sodium silicate ($Na_2O \cdot 3.1SiO_2$) containing 95 g/kg of $SiO_2$ and 25 g/kg of NaCl and then, under the reaction temperature kept at 87° C., 10% sulfuric acid at the flow rate of 10.1 kg/min for 96 minutes to bring the pH of the reaction mixture to 10.0. Then the addition of 10% sulfuric acid was continued at the flow rate of 17.9 kg/min until 28 minutes later when the pH reached 1.8. The acid was stopped and the reaction mixture was allowed to stand for ageing for 15 minutes. After repeated filtration and washing, part of the wet cake was dried in a hot air oven at 110° C. and finely ground.

The fine silica powder thus obtained had a specific surface area by the BET method of 293 $m^2/g$ and by the CTAB method of 16 $m^2/g$; it gave an amorphous X-ray diffraction pattern after being fired at 1100° C.; it had an abrasiveness value of 26.1 mg, a refractive index of 1.462 and a lowest turbidity of 0.020; and it proved to be a product of high abrasiveness and long-lasting transparency.

EXAMPLE 2

Into a 20 l reactor equipped with a baffle plate and an agitator with 150 mm D turbine blades were introduced 10 kg of sodium silicate solution ($Na_2O.2.8SiO_2$) containing 100 g/kg of $SiO_2$ and 35 g/kg of NaCl and then, under the reaction temperature kept at 80° C., 10% sulfuric acid at the flow rate of 97 g/min for 42 minutes to bring the pH of the reaction mixture to 10.0. Then the addition of 10% sulfuric acid was continued at 148 g/min until 14 minutes later when the pH reached 2.2. The acid was stopped and the reaction mixture was allowed to stand for ageing for 15 minutes. After repeated filtration and washing, the obtained solid was dried in a hot air oven at 110° C. and finely ground. The fine silica powder thus obtained had a specific surface area by the BET method of 315 $m^2/g$ and by CTAB method of 28 $m^2/g$; it gave an amorphous X-ray diffraction pattern after being fired at 1100° C.; it had an abrasiveness value of 19.5 mg, a refractive index of 1.462 and a lowest turbidity of 0.028; and it proved to be a product of moderate abrasiveness and long-lasting transparency.

EXAMPLE 3

Into a 10 l reactor equipped with a baffle plate and an agitator with 100 mm D turbine blades was introduced 4.5 kg of an aqueous solution of potassium silicate ($K_2O.3.0SiO_2$) containing 100 g/kg of $SiO_2$ and 20 g/kg of $K_2SO_4$ and then, under the reaction temperature kept at 75° C., 8% hydrochloric acid at the flow rate of 12.7 g/min for 126 minutes to bring the pH of the reaction mixture to 10.0. Then the addition of 8% hydrochloric acid was continued at 31.8 g/min until 25 minutes later when the pH reached 2.3. The acid was stopped and the reaction mixture was allowed to stand for ageing for 20 minutes. After repeated filtration and washing, the obtained solid was dried in a hot air oven at 110° C. and finely ground.

The fine silica powder thus ablained had a specific surface area by the BET method of 286 $m^2/g$ and by the CTAB method of 23 $m^2/g$; it gave an amorphous X-ray diffraction pattern after being fired at 1100° C.; it had an abrasiveness value of 12.3 mg, a refractive index of 1.461 and a lowest turbidity of 0.018; and it proved to be a product of moderate abrasiveness and long-lasting transparency.

The examples given above clearly show that the product of the present invention has excellent characteristics as a base material for transparent dentifrice formulations. But in order to show more concretely the longevity of transparency it gives to such formulations, turbidity change was traced for three paste formulations each containing 25% the silica powder mentioned in the corresponding example and having a refractive index adjusted to 1.463. The results were as shown in Table 2.

TABLE 2

| Example | Turbidity just after formulation | Turbidity after one month |
|---|---|---|
| 1 | 0.035 | 0.030 |
| 2 | 0.038 | 0.042 |
| 3 | 0.053 | 0.048 |

COMPARISON 1

Table 3 shows the levels of refractive index and turbidity of two brands of commercially available toothpaste for the sake of reference.

TABLE 3

| Commercial transparent toothpaste | Refractive index | Turbidity |
|---|---|---|
| Brand A (made in USA) | 1.4600 | 0.321 |
| Brand B (made in USA) | 1.4593 | 0.274 |

Comparison of Table 3 and other data cited hereinbefore reveals clearly that the transparent toothpaste formulations now commercially available are substantially less transparent than the corresponding formulations using the silica base material of the present invention.

We claim:

1. A method for production of a silica base material for a dentifrice formulation, which comprises reacting an alkali metal silicate solution and hydrochloric or sulfuric acid in the presence of an electrolyte in two stages, namely a silica crystallization stage for which the pH of reaction mixture is brought to 10.0, and an acidification stage for which the pH is finally brought down to 3.5 or less, and wherein the ratio of the rate of addition of chloride or sulfate ion in the acidification stage to the rate of said addition in the silica crystallization stage is at least 3:2, and the acidification is carried out within 30 minutes; said silica base material having a specific surface area by the BET method of 270–500 $m^2$/g-anhydride, and by the CTAB method of 5–60 $m^2$/g-anhydride, giving amorphous X-ray diffraction patterns after firing at 1100° C., and having a refractive index of 1.455–1.470.

2. The method described in claim 1, where the electrolyte is previously added to the alkali metal silicate solution.

3. The method described in claim 1, where the alkali metal silicate solution has a molar ratio, $SiO_2/X_2O$ wherein X denotes alkali metal, of 2–4.

4. The method described in claim 1, where the $SiO_2$ concentration of the alkali metal silicate solution before the addition of hydrochloric or sulfuric acid is 5–15% by weight.

5. The method described in claim 1, where the electrolyte is an alkali metal salt of a mineral acid.

6. The method described in claim 1, where the amount of the electrolyte is 10–60% by weight of $SiO_2$.

7. The method described in claim 1, where the concentration of hydrochloric or sulfuric acid is 5–15% by weight.

8. The method described in claim 1, where the reaction temperature during the silica crystallization stage is 60°–100° C.

9. The method described in claim 1, where the addition of hydrochloric or sulfuric acid during the silica crystallization stage is conducted for 40 minutes to 4 hours.

* * * * *